US007645920B1

(12) United States Patent
Renard et al.

(10) Patent No.: US 7,645,920 B1
(45) Date of Patent: Jan. 12, 2010

(54) MUTANT GENE OF THE GRAS FAMILY AND PLANTS WITH REDUCED DEVELOPMENT CONTAINING SAID MUTANT GENE

(75) Inventors: Michel Renard, Le Rheu (FR); Regine Delourme, L'Hermitage (FR); Pierre Barret, Clermont-Ferrand (FR); Dominique Brunel, Paris (FR); Nicole Froger, Saint-Cyr-l'Ecole (FR); Xavier Tanguy, Moigne le Rheu (FR)

(73) Assignee: Institut National de la Recherche Agronomique (INRA), Paris (FR)

( * ) Notice: Subject to any disclaimer, the term of this patent is extended or adjusted under 35 U.S.C. 154(b) by 517 days.

(21) Appl. No.: 10/030,194

(22) PCT Filed: Aug. 2, 2000

(86) PCT No.: PCT/FR00/02216

§ 371 (c)(1),
(2), (4) Date: Aug. 15, 2002

(87) PCT Pub. No.: WO01/09356

PCT Pub. Date: Feb. 8, 2001

(30) Foreign Application Priority Data

Aug. 2, 1999 (FR) .................................. 99 10023

(51) Int. Cl.
*C12N 15/29* (2006.01)
*A01H 5/00* (2006.01)
*A01H 5/10* (2006.01)

(52) U.S. Cl. ........................ 800/298; 800/306; 800/276; 536/23.6

(58) Field of Classification Search ................ 536/23.1, 536/23.6; 800/278, 298, 290, 306
See application file for complete search history.

(56) References Cited

FOREIGN PATENT DOCUMENTS

WO  97 29123  8/1997
WO  99 09174  2/1999

OTHER PUBLICATIONS

Kano-Murakami et al (1993, FEBS 334:365-368).*
Peng et al (1997, Genes & Development 11:3194-3205).*
Foisset et al (1995, Theor. Appl. Genet. 91(5):756-761).*
Pysh et al (1999, The Plant Journal 18(1):111-119).*
Schumacher et al (1999, PNAS 96:290-295).*
Peng et al (Nature, Jul. 15, 1999 400:256-261).*
Merriam-Webster Dictionary, on-line, 2006.*
Campbell et al (Ed's), 2002, Biology, 6th Edition, Benjamin Cunnings, Publisher, New York, p. 73.*
Barret et al (1998, Theor. Appl. Genet. 97:828-833).*
Yang et al (2001, PNAS 98(20):11438-11443).*
Riechmann et al (2000, Current Opinion in Plant Biology 3:423-434).*

Jaglo et al (2001, Plant Physiology 127:910-917).*
Merriam Webster Online Dictionary. 2008.*
Troung et al.: "Sequence and characterization of two *Arabidopsis thaliana* cDNAs isolated by funtional complementation of a yeast gln3 gdh1 mutant" FEBS Letters, vol. 410, pp. 213-218 Jun. 1, 1997.
M.J. May: "Cloning of the *Arabidopsis thaliana* RGA-like gene, a putative member of the VHIID domain transcription factor family" Database TREMBL , EMBL Heidelberg, Germany AC/ID 065367 Aug. 1, 1998.
N. Foisset et al.: "Molecular tagging of the dwarf Breizh (Bzh) gene in *Brassica napus*" Theoretical and Applied Genetics, vol. 91, No. 5, pp. 756-761 Oct. 1995.
L.D. Pysh, et al., "The GRAS Gene Family in *Arabidopsis*: Sequence Characterization and Basic Expression Analysis of the Scarecrow-Like Genes", The Plant Journal, vol. 18, No. 1, 1999, pp. 111-119.
K. Schumacher, et al., "The Lateral Suppressor (LS) Gene of Tomato Encodes a New Member of the VHIID Protein Family", Proc. Natl. Acad. Sci. USA, vol. 96, Jan. 1999, pp. 290-295.
J. Peng, et al., "Green Revolution Genes Encode Mutant Gibberellin Response Modulators", Nature, vol. 400, Jul. 15, 1999, pp. 256-261.
Silverstone, A. L., et al., "The *Arabidopsis* RGA Gene Encodes a Transcriptional Regulator Repressing the Gibberellin Signal Transduction Pathway," American Society of Plant Physiologists, The Plant Cell, vol. 10, Feb. 1998, pp. 155-169.
Dill, et al., "The DELLA Motif is Essential for Gibberellin-Induced Degradation of RCA," Proc. Natl. Acad. Sci. USA, 98, 2001, pp. 14162-14167 (Abstract Only).
Ikeda, et al., Slender Rice, A Constitutive Gibberellin Response Mutant, Is Caused By a Null Mutation of the SLR1 Gene, An Ortholog of the Height-Regulating Gene GA1/RGA/RHT/D8, Place Cell, 18, 2001, pp. 999-1010 (Abstract Only).
Boss, et al., "Association of Dwarfism and Floral Induction with a Grape 'Green Revolution' Mutation," Nature, 416, 2002, pp. 847-850 (Abstract Only).
Chandler, et al., "Mutants at the Slender1 Locus of Barley CV Himalaya. Molecular and Physiological Characterization," Plant Physiol, 129, 2002, pp. 181-190 (Abstract Only).
Wen, et al., "*Arabidopsis* RGL1 Encodes A Negative Regulator of Gibberellin Responses," Plance Cell, 14, 2002, pp. 87-100 (Abstract Only).
Muangprom, et al., "A Novel Dwarfing Mutation In a Green Revolution Gene From *Brassica Rapa*," Plant Physiol, 137, 2005, pp. 931-938 (Abstract Only).
Busov, et al., "Transgenic Modification of Gai or RGL1 Causes Dwarfing and Alters Gibberellins, Root Growth, and Metabolite Profiles in Populus," Planta, 224, 2006, pp. 288-299 (Abstract Only).
Olszewski, N., et al., "Gibberellin Signaling: Biosynthesis, Catabolism, and Response Pathways," American Society of Plant Biologists, The Plant Cell, Supplemental 2002, pp. S61-S80.
Muangprom, A., et al., "A Novel Dwarfing Mutation In A Green Revolution Gene From *Brassica Rapa*$_1$," American Society of Plant Biologists, Plant Physiology, vol. 137, Mar. 2005, pp. 931-938.

* cited by examiner

*Primary Examiner*—Stuart F. Baum
(74) *Attorney, Agent, or Firm*—Oblon, Spivak, McClelland, Maier & Neustadt, L.L.P.

(57) ABSTRACT

The invention relates to the production of plants with reduced development and a mutant gene of the GRAS family.

8 Claims, 2 Drawing Sheets

Figure 1

```
             501
(GAI)        PPVFRLTGIG PPAPDNFDYL HEVGCKLAHL AEAIHVEFEY RG.FVANTLA DLDA......S MLELRPSEIE SVAVNSVFEL HKLLGRPGAI DKVLGVVNQI
(RGA)        PPVFRLTGIG PPAPDNFDYL HEVGCKLAHL AEAIHVEFEY RG.FVANTLA DLDA......S MLELRPSEIE SVAVNSVFEL HKLLGRPGAI DKVLGVVNQI
(BZH-sauvage) PPSFRLTGIG PPAADNSDHL HEVGCKLAQL AEAIHVEFEY RG.FVANSLA DLDA......S MLELRPSETE AVAVNSVFEL HKLLGRTGI  EKVFGVVKQI
(RGAL)       PPDFRLTGIG YSLTD.....I QEVGWKLGQL ASTIGVNFEF KS.IALNNLS DLKP......E MLDIRPG..LE SVAVNSVFEL HRLLAHPGSI DKFLSTIKSI
(LS)         .PTLRITGTG .....NDLDTL RRTGDRLAKF AHSLGLREQF HPLYIANNNH DHDEDPSIIS SIVLLPD..E TLAINCVFYL HRLLKDREKL RIFLHRVKSM
(SCARECROW)  PHVRLTGLG  .....TSMEAL QATGKRLSDF TDKLGLPFEF CP..LAEKVG NLD......TE RLNVR..KRE AVAVH..WLQ HSLYDVTGSD AHTIWLLQRL
                                                                                                                        600

601
(GAI)        KPEIFTVVEQ ESNHNSPIFL DRFTESLHYY STLFDSLEG. .VPSGQDKV. MSEVYLGKQI CNVVACDGPD RVERHETLSQ WRNRFGSAGF AAAHIGSNAF
(RGA)        KPEIFTVVEQ ESNHNSPIFL DRFTESLHYY STLFDSLEG. .VPSGQDKV. MSEVYLGKQI CNVVACDGPD RVERHETLSQ WRNRFGSAGF AAAHIGSNAF
(BZH-sauvage) KPVIFTVVEQ ESNHNGPVFL DRFTESLHYY STLFDSLEG. .APSSQDKV. MSEVYLGKQI CNLVACEGPD RVERHETLSQ WSNRFGSSGF APAHLGSNAF
(RGAL)       RPDIMTVVEQ EANHNGTVFL DRFTESLHYY SSLFDSLEG. .PPS.QDRV. MSELFLGRQI LNLVACEGED RVERHETLNQ WRNRFGLGGF KPVSIGSNAY
(LS)         NPKIVTIAEK EANHNHPLFL QRFIEALDYY TAVFDSLEAT LPPGSRERMT VEQWFGREI  VDIVAMEGDK RKERHERFRS WEVMLRSCGF SNVALSPFAL
(SCARECROW)  APKVVTVVEQ DLSHAGS.FL GRFVEAIHYY SALFDSLGAS YGEESEERHV VEQQLLSKEI RNVLAVGGPS R.SGEVKFES WREKMQQCGF KGISLAGNAA
                                                                                                                        700

701                                                    746
(GAI)        KQASMLLALF NGGEGYRVEE SDGCLMLGWH TRPLIATSAW KLSTN~
(RGA)        KQASMLLALF NGGEGYRVEE SDGCLMLGWH TRPLIATSAW KLSTN~
(BZH-sauvage) KQASTLLALF NGGEGYRVEE NNGCLMLSWH TRPLITTSAW KLSAVH
(RGAL)       KQASMLLALY AGADGYNVEE NEGCLLLGWQ TRPLIATSAW RINRVE
(LS)         SQAKLLLRLH YPSEGYQLGV SSNSFFLGWQ NQPLFSISSW R~~~~~
(SCARECROW)  TQATLLLGMF .PSDGYTLVD DNGTLKLGWK DLSLLTASAW TPRS~~
```

Figure 1 (suite)

SEQUENCE LISTING

<160> NUMBER OF SEQ ID NOS: 7

<210> SEQ ID NO 1
<211> LENGTH: 1779
<212> TYPE: DNA
<213> ORGANISM: Brassica napus
<220> FEATURE:
<221> NAME/KEY: CDS
<222> LOCATION: (60)..(1778)

<400> SEQUENCE: 1

```
caacccagaa caaaaccaga ccgatctgag agattaacta tatcttaacc agatcagaa        59 atg aag agg gat ctt cat cag ttc caa ggt ccc aac cac ggg aca tca       107
Met Lys Arg Asp Leu His Gln Phe Gln Gly Pro Asn His Gly Thr Ser
 1               5                  10                  15 atc gcc ggt tct tcc act tct tcc cct gcg gtg ttt ggt aaa gac aag       155
Ile Ala Gly Ser Ser Thr Ser Ser Pro Ala Val Phe Gly Lys Asp Lys
             20                  25                  30 atg atg atg gtc aaa gaa gaa gaa gac gac gag ctt cta gga gtc ttg       203
Met Met Met Val Lys Glu Glu Glu Asp Asp Glu Leu Leu Gly Val Leu
         35                  40                  45 ggt tac aag gtt agg tct tcg gag atg gct gag gtt gcg ttg aaa ctc       251
Gly Tyr Lys Val Arg Ser Ser Glu Met Ala Glu Val Ala Leu Lys Leu
 50                  55                  60 gag cag ctt gag acg atg atg ggt aac gct caa gaa gac ggt tta gct       299
Glu Gln Leu Glu Thr Met Met Gly Asn Ala Gln Glu Asp Gly Leu Ala
 65                  70                  75                  80 cac ctc gcg acg gat act gtt cat tac aac ccc gct gag ctt tac tcg       347
His Leu Ala Thr Asp Thr Val His Tyr Asn Pro Ala Glu Leu Tyr Ser
                 85                  90                  95 tgg ctt gat aac atg ctc acg gag ctt aac cca ccc gct gca acg acc       395
Trp Leu Asp Asn Met Leu Thr Glu Leu Asn Pro Pro Ala Ala Thr Thr
            100                 105                 110 gga tct aac gct ttg aac ccg gag att aat aat aat aat aat aac tcg       443
Gly Ser Asn Ala Leu Asn Pro Glu Ile Asn Asn Asn Asn Asn Asn Ser
        115                 120                 125 ttt ttc acc gga ggc gac ctc aaa gcg att cct gga aac gcg gtt tgt       491
Phe Phe Thr Gly Gly Asp Leu Lys Ala Ile Pro Gly Asn Ala Val Cys
    130                 135                 140 cgc aga tct aat cag ttc gcg ttt gcg gtt gat tcg tcg agt aat aag       539
Arg Arg Ser Asn Gln Phe Ala Phe Ala Val Asp Ser Ser Ser Asn Lys
145                 150                 155                 160 cgt ttg aaa ccg tcc tcg agc cct gat tcg atg gtt aca tct cca tca       587
Arg Leu Lys Pro Ser Ser Ser Pro Asp Ser Met Val Thr Ser Pro Ser
                165                 170                 175 cct gct gga gtt ata gga acg acg gtt aca acc gtg acc gag tca act       635
Pro Ala Gly Val Ile Gly Thr Thr Val Thr Thr Val Thr Glu Ser Thr
            180                 185                 190 cgt cct tta atc ctg gtc gac tcg cag gac aac gga gtg cgt cta gtc       683
Arg Pro Leu Ile Leu Val Asp Ser Gln Asp Asn Gly Val Arg Leu Val
        195                 200                 205 cac gcg ctt atg gcc tgc gct gaa gcc gtg cag agc agc aac ttg act       731
His Ala Leu Met Ala Cys Ala Glu Ala Val Gln Ser Ser Asn Leu Thr
    210                 215                 220 cta gcg gag gct ctc gtt aag cag att ggt ttc ttg gcc gtc tct caa       779
Leu Ala Glu Ala Leu Val Lys Gln Ile Gly Phe Leu Ala Val Ser Gln
225                 230                 235                 240 gcc gga gcc atg agg aaa gtc gcc acg tac ttc gcc gaa gct ctc gcg       827
Ala Gly Ala Met Arg Lys Val Ala Thr Tyr Phe Ala Glu Ala Leu Ala
```

-continued

```
                245                 250                 255
cgg agg atc tac cgc ctc tct ccg ccg cag acg cag atc gat cac tct     875
Arg Arg Ile Tyr Arg Leu Ser Pro Pro Gln Thr Gln Ile Asp His Ser
            260                 265                 270 tta tcc gat act ctc cag atg cac ttc tac gag act tgc cct tac ctc     923
Leu Ser Asp Thr Leu Gln Met His Phe Tyr Glu Thr Cys Pro Tyr Leu
            275                 280                 285 aag ttc gct cac ttc acg gcg aat cag gcg att ctc gag gct ttc gaa     971
Lys Phe Ala His Phe Thr Ala Asn Gln Ala Ile Leu Glu Ala Phe Glu
            290                 295                 300 ggg aag aag aga gtc cac gtc atc gat ttc tcg atg aac caa ggg ctt    1019
Gly Lys Lys Arg Val His Val Ile Asp Phe Ser Met Asn Gln Gly Leu
305                 310                 315                 320 cag tgg ccc gcg ctt atg caa gcc ctt gcg ttg agg gaa gga ggt cct    1067
Gln Trp Pro Ala Leu Met Gln Ala Leu Ala Leu Arg Glu Gly Gly Pro
            325                 330                 335 ccg agt ttc agg tta acc gga att ggt cct ccc gcg gcg gat aac tcc    1115
Pro Ser Phe Arg Leu Thr Gly Ile Gly Pro Pro Ala Ala Asp Asn Ser
            340                 345                 350 gat cat ctc cat gaa gtt gga tgt aag ttg gct cag ctc gcg gag gcg    1163
Asp His Leu His Glu Val Gly Cys Lys Leu Ala Gln Leu Ala Glu Ala
            355                 360                 365 att cac gtc gag ttt gag tat cgt ggc ttt gtt gct aat agc tta gct    1211
Ile His Val Glu Phe Glu Tyr Arg Gly Phe Val Ala Asn Ser Leu Ala
            370                 375                 380 gat ctt gat gcc tcg atg ctt gag ctt aga ccg agt gaa acc gaa gct    1259
Asp Leu Asp Ala Ser Met Leu Glu Leu Arg Pro Ser Glu Thr Glu Ala
385                 390                 395                 400 gtg gcg gtt aac tct gtt ttc gag ctc cac aag ctc cta ggc cgt acc    1307
Val Ala Val Asn Ser Val Phe Glu Leu His Lys Leu Leu Gly Arg Thr
            405                 410                 415 ggt ggg ata gag aaa gtc ttc ggc gtt gtg aaa cag att aaa ccg gtg    1355
Gly Gly Ile Glu Lys Val Phe Gly Val Val Lys Gln Ile Lys Pro Val
            420                 425                 430 att ttc acg gtt gtt gag caa gaa tcg aat cat aac ggt ccg gtt ttc    1403
Ile Phe Thr Val Val Glu Gln Glu Ser Asn His Asn Gly Pro Val Phe
            435                 440                 445 tta gac cgg ttt act gaa tcg ctg cat tat tat tcg acg ttg ttt gat    1451
Leu Asp Arg Phe Thr Glu Ser Leu His Tyr Tyr Ser Thr Leu Phe Asp
450                 455                 460 tcc ttg gaa ggt gct ccg agt agc caa gat aaa gtt atg tcg gaa gtt    1499
Ser Leu Glu Gly Ala Pro Ser Ser Gln Asp Lys Val Met Ser Glu Val
465                 470                 475                 480 tat tta ggg aaa cag att tgc aat ctg gtg gct tgc gaa ggt ccg gac    1547
Tyr Leu Gly Lys Gln Ile Cys Asn Leu Val Ala Cys Glu Gly Pro Asp
            485                 490                 495 cgt gtt gag aga cat gag acg ctg agt caa tgg tcg aac cgg ttc ggt    1595
Arg Val Glu Arg His Glu Thr Leu Ser Gln Trp Ser Asn Arg Phe Gly
            500                 505                 510 tcg tcc ggt ttt gcg ccg gcg cat ctc ggg tct aac gcg ttt aag caa    1643
Ser Ser Gly Phe Ala Pro Ala His Leu Gly Ser Asn Ala Phe Lys Gln
            515                 520                 525 gcg agt acg ctt ttg gct ttg ttt aat gga ggc gaa ggt tat cgt gtg    1691
Ala Ser Thr Leu Leu Ala Leu Phe Asn Gly Gly Glu Gly Tyr Arg Val
            530                 535                 540 gag gag aat aat ggg tgt ttg atg ttg agt tgg cac act cga ccg ctc    1739
Glu Glu Asn Asn Gly Cys Leu Met Leu Ser Trp His Thr Arg Pro Leu
545                 550                 555                 560 ata acc acc tcc gct tgg aag ctc tcg gcg gtg cac tga g              1779
Ile Thr Thr Ser Ala Trp Lys Leu Ser Ala Val His
```

```
Ile Thr Thr Ser Ala Trp Lys Leu Ser Ala Val His
            565                 570
```

<210> SEQ ID NO 2
<211> LENGTH: 572
<212> TYPE: PRT
<213> ORGANISM: Brassica napus

<400> SEQUENCE: 2

```
Met Lys Arg Asp Leu His Gln Phe Gln Gly Pro Asn His Gly Thr Ser
1               5                   10                  15

Ile Ala Gly Ser Ser Thr Ser Ser Pro Ala Val Phe Gly Lys Asp Lys
            20                  25                  30

Met Met Met Val Lys Glu Glu Asp Asp Glu Leu Leu Gly Val Leu
            35                  40                  45

Gly Tyr Lys Val Arg Ser Ser Glu Met Ala Glu Val Ala Leu Lys Leu
50                  55                  60

Glu Gln Leu Glu Thr Met Met Gly Asn Ala Gln Glu Asp Gly Leu Ala
65                  70                  75                  80

His Leu Ala Thr Asp Thr Val His Tyr Asn Pro Ala Glu Leu Tyr Ser
            85                  90                  95

Trp Leu Asp Asn Met Leu Thr Glu Leu Asn Pro Pro Ala Ala Thr Thr
            100                 105                 110

Gly Ser Asn Ala Leu Asn Pro Glu Ile Asn Asn Asn Asn Asn Ser
            115                 120                 125

Phe Phe Thr Gly Gly Asp Leu Lys Ala Ile Pro Gly Asn Ala Val Cys
            130                 135                 140

Arg Arg Ser Asn Gln Phe Ala Phe Ala Val Asp Ser Ser Ser Asn Lys
145                 150                 155                 160

Arg Leu Lys Pro Ser Ser Pro Asp Ser Met Val Thr Ser Pro Ser
            165                 170                 175

Pro Ala Gly Val Ile Gly Thr Thr Thr Thr Val Thr Glu Ser Thr
            180                 185                 190

Arg Pro Leu Ile Leu Val Asp Ser Gln Asp Asn Gly Val Arg Leu Val
            195                 200                 205

His Ala Leu Met Ala Cys Ala Glu Ala Val Gln Ser Ser Asn Leu Thr
210                 215                 220

Leu Ala Glu Ala Leu Val Lys Gln Ile Gly Phe Leu Ala Val Ser Gln
225                 230                 235                 240

Ala Gly Ala Met Arg Lys Val Ala Thr Tyr Phe Ala Glu Ala Leu Ala
            245                 250                 255

Arg Arg Ile Tyr Arg Leu Ser Pro Pro Gln Thr Gln Ile Asp His Ser
            260                 265                 270

Leu Ser Asp Thr Leu Gln Met His Phe Tyr Glu Thr Cys Pro Tyr Leu
            275                 280                 285

Lys Phe Ala His Phe Thr Ala Asn Gln Ala Ile Leu Glu Ala Phe Glu
            290                 295                 300

Gly Lys Lys Arg Val His Val Ile Asp Phe Ser Met Asn Gln Gly Leu
305                 310                 315                 320

Gln Trp Pro Ala Leu Met Gln Ala Leu Ala Leu Arg Glu Gly Gly Pro
            325                 330                 335

Pro Ser Phe Arg Leu Thr Gly Ile Gly Pro Pro Ala Ala Asp Asn Ser
            340                 345                 350

Asp His Leu His Glu Val Gly Cys Lys Leu Ala Gln Leu Ala Glu Ala
            355                 360                 365
```

```
Ile His Val Glu Phe Glu Tyr Arg Gly Phe Val Ala Asn Ser Leu Ala
    370             375             380

Asp Leu Asp Ala Ser Met Leu Glu Leu Arg Pro Ser Glu Thr Glu Ala
385             390             395             400

Val Ala Val Asn Ser Val Phe Glu Leu His Lys Leu Leu Gly Arg Thr
                405             410             415

Gly Gly Ile Glu Lys Val Phe Gly Val Val Lys Gln Ile Lys Pro Val
            420             425             430

Ile Phe Thr Val Val Glu Gln Glu Ser Asn His Asn Gly Pro Val Phe
        435             440             445

Leu Asp Arg Phe Thr Glu Ser Leu His Tyr Tyr Ser Thr Leu Phe Asp
    450             455             460

Ser Leu Glu Gly Ala Pro Ser Ser Gln Asp Lys Val Met Ser Glu Val
465             470             475             480

Tyr Leu Gly Lys Gln Ile Cys Asn Leu Val Ala Cys Glu Gly Pro Asp
                485             490             495

Arg Val Glu Arg His Glu Thr Leu Ser Gln Trp Ser Asn Arg Phe Gly
            500             505             510

Ser Ser Gly Phe Ala Pro Ala His Leu Gly Ser Asn Ala Phe Lys Gln
        515             520             525

Ala Ser Thr Leu Leu Ala Leu Phe Asn Gly Gly Glu Gly Tyr Arg Val
    530             535             540

Glu Glu Asn Asn Gly Cys Leu Met Leu Ser Trp His Thr Arg Pro Leu
545             550             555             560

Ile Thr Thr Ser Ala Trp Lys Leu Ser Ala Val His
                565             570

<210> SEQ ID NO 3
<211> LENGTH: 1779
<212> TYPE: DNA
<213> ORGANISM: Brassica napus
<220> FEATURE:
<221> NAME/KEY: CDS
<222> LOCATION: (60)..(1778)

<400> SEQUENCE: 3
caacccagaa caaaaccaga ccgatctgag agattaacta tatcttaacc agatcagaa        59 atg aag agg gat ctt cat cag ttc caa ggt ccc aac cac ggg aca tca      107
Met Lys Arg Asp Leu His Gln Phe Gln Gly Pro Asn His Gly Thr Ser
1               5                  10                  15 atc gcc ggt tct tcc act tct tcc cct gcg gtg ttt ggt aaa gac aag      155
Ile Ala Gly Ser Ser Thr Ser Ser Pro Ala Val Phe Gly Lys Asp Lys
                20                  25                  30 atg atg atg gtc aaa gaa gaa gaa gac gac gag ctt cta gga gtc ttg      203
Met Met Met Val Lys Glu Glu Glu Asp Asp Glu Leu Leu Gly Val Leu
            35                  40                  45 ggt tac aag gtt agg tct tcg gag atg gct gag gtt gcg ttg aaa ctc      251
Gly Tyr Lys Val Arg Ser Ser Glu Met Ala Glu Val Ala Leu Lys Leu
        50                  55                  60 gag cag ctt gag acg atg atg ggt aac gct caa gaa gac ggt tta gct      299
Glu Gln Leu Glu Thr Met Met Gly Asn Ala Gln Glu Asp Gly Leu Ala
65                  70                  75                  80 cac ctc gcg acg gat act gtt cat tac aac ccc gct gag ctt tac tcg      347
His Leu Ala Thr Asp Thr Val His Tyr Asn Pro Ala Glu Leu Tyr Ser
                85                  90                  95 tgg ctt gat aac atg ctc acg gag ctt aac cca ccc gct gca acg acc      395
Trp Leu Asp Asn Met Leu Thr Glu Leu Asn Pro Pro Ala Ala Thr Thr
```

-continued

```
                100                 105                 110
gga tct aac gct ttg aac ccg gag att aat aat aat aat aac tcg      443
Gly Ser Asn Ala Leu Asn Pro Glu Ile Asn Asn Asn Asn Asn Ser
        115                 120                 125 ttt ttc acc gga ggc gac ctc aaa gcg att cct gga aac gcg gtt tgt  491
Phe Phe Thr Gly Gly Asp Leu Lys Ala Ile Pro Gly Asn Ala Val Cys
130                 135                 140 cgc aga tct aat cag ttc gcg ttt gcg gtt gat tcg tcg agt aat aag  539
Arg Arg Ser Asn Gln Phe Ala Phe Ala Val Asp Ser Ser Ser Asn Lys
145                 150                 155                 160 cgt ttg aaa ccg tcc tcg agc cct gat tcg atg gtt aca tct cca tca  587
Arg Leu Lys Pro Ser Ser Ser Pro Asp Ser Met Val Thr Ser Pro Ser
                165                 170                 175 cct gct gga gtt ata gga acg acg gtt aca acc gtg acc gag tca act  635
Pro Ala Gly Val Ile Gly Thr Thr Val Thr Thr Val Thr Glu Ser Thr
            180                 185                 190 cgt cct tta atc ctg gtc gac tcg cag gac aac gga gtg cgt cta gtc  683
Arg Pro Leu Ile Leu Val Asp Ser Gln Asp Asn Gly Val Arg Leu Val
        195                 200                 205 cac gcg ctt atg gcc tgc gct gaa gcc gtg cag agc agc aac ttg act  731
His Ala Leu Met Ala Cys Ala Glu Ala Val Gln Ser Ser Asn Leu Thr
    210                 215                 220 cta gcg gag gct ctc gtt aag cag att ggt ttc ttg gcc gtc tct caa  779
Leu Ala Glu Ala Leu Val Lys Gln Ile Gly Phe Leu Ala Val Ser Gln
225                 230                 235                 240 gcc gga gcc atg agg aaa gtc gcc acg tac ttc gcc gaa gct ctc gcg  827
Ala Gly Ala Met Arg Lys Val Ala Thr Tyr Phe Ala Glu Ala Leu Ala
                245                 250                 255 cgg agg atc tac cgc ctc tct ccg ccg cag acg cag atc gat cac tct  875
Arg Arg Ile Tyr Arg Leu Ser Pro Pro Gln Thr Gln Ile Asp His Ser
            260                 265                 270 tta tcc gat act ctc cag atg cac ttc tac gag act tgc cct tac ctc  923
Leu Ser Asp Thr Leu Gln Met His Phe Tyr Glu Thr Cys Pro Tyr Leu
        275                 280                 285 aag ttc gct cac ttc acg gcg aat cag gcg att ctc gag gct ttc gaa  971
Lys Phe Ala His Phe Thr Ala Asn Gln Ala Ile Leu Glu Ala Phe Glu
    290                 295                 300 ggg aag aag aga gtc cac gtc atc gat ttc tcg atg aac caa ggg ctt  1019
Gly Lys Lys Arg Val His Val Ile Asp Phe Ser Met Asn Gln Gly Leu
305                 310                 315                 320 cag tgg ccc gcg ctt atg caa gcc ctt gcg ttg agg gaa gga ggt cct  1067
Gln Trp Pro Ala Leu Met Gln Ala Leu Ala Leu Arg Glu Gly Gly Pro
                325                 330                 335 ccg agt ttc agg tta acc gga att ggt cct ccc gcg gcg gat aac tcc  1115
Pro Ser Phe Arg Leu Thr Gly Ile Gly Pro Pro Ala Ala Asp Asn Ser
            340                 345                 350 gat cat ctc cat gaa gtt gga tgt aag ttg gct cag ctc gcg gag gcg  1163
Asp His Leu His Glu Val Gly Cys Lys Leu Ala Gln Leu Ala Glu Ala
        355                 360                 365 att cac gtc gag ttt gag tat cgt ggc ttt gtt gct aat agc tta gct  1211
Ile His Val Glu Phe Glu Tyr Arg Gly Phe Val Ala Asn Ser Leu Ala
    370                 375                 380 gat ctt gat gcc tcg atg ctt gag ctt aga ccg agt gaa acc gaa gct  1259
Asp Leu Asp Ala Ser Met Leu Glu Leu Arg Pro Ser Glu Thr Glu Ala
385                 390                 395                 400 gtg gcg gtt aac tct gtt ttc gag ctc cac aag ctc cta ggc cgt acc  1307
Val Ala Val Asn Ser Val Phe Glu Leu His Lys Leu Leu Gly Arg Thr
                405                 410                 415 ggt ggg ata gag aaa gtc ttc ggc gtt gtg aaa cag att aaa ccg gtg  1355
```

-continued

```
          Gly Gly Ile Glu Lys Val Phe Gly Val Val Lys Gln Ile Lys Pro Val
                      420                 425                 430 att ttc acg gtt gtt gag caa gaa tcg aat cat aac ggt ccg gtt ttc           1403
Ile Phe Thr Val Val Glu Gln Glu Ser Asn His Asn Gly Pro Val Phe
            435                 440                 445 tta gac cgg ttt act gaa tcg ctg cat tat tat tcg acg ttg ttt gat           1451
Leu Asp Arg Phe Thr Glu Ser Leu His Tyr Tyr Ser Thr Leu Phe Asp
        450                 455                 460 tcc ttg gaa ggt gct ccg agt agc caa gat aaa gtt atg tcg gaa gtt           1499
Ser Leu Glu Gly Ala Pro Ser Ser Gln Asp Lys Val Met Ser Glu Val
465                 470                 475                 480 tat tta ggg aaa cag att tgc aat ctg gtg gct tgc gaa ggt ccg gac           1547
Tyr Leu Gly Lys Gln Ile Cys Asn Leu Val Ala Cys Glu Gly Pro Asp
                485                 490                 495 cgt gtt gag aga cat gag acg ctg agt caa tgg tcg aac cgg ttc ggt           1595
Arg Val Glu Arg His Glu Thr Leu Ser Gln Trp Ser Asn Arg Phe Gly
            500                 505                 510 tcg tcc ggt ttt gcg ccg gcg cat ctc ggg tct aac gcg ttt aag caa           1643
Ser Ser Gly Phe Ala Pro Ala His Leu Gly Ser Asn Ala Phe Lys Gln
        515                 520                 525 gcg agt acg ctt ttg gct ttg ttt aat gga ggc gaa ggt tat cgt gtg           1691
Ala Ser Thr Leu Leu Ala Leu Phe Asn Gly Gly Glu Gly Tyr Arg Val
530                 535                 540 gag aag aat aat ggg tgt ttg atg ttg agt tgg cac act cga ccg ctc           1739
Glu Lys Asn Asn Gly Cys Leu Met Leu Ser Trp His Thr Arg Pro Leu
545                 550                 555                 560 ata acc acc tcc gct tgg aag ctc tcg gcg gtg cac tga g                     1779
Ile Thr Thr Ser Ala Trp Lys Leu Ser Ala Val His
                565                 570

<210> SEQ ID NO 4
<211> LENGTH: 572
<212> TYPE: PRT
<213> ORGANISM: Brassica napus

<400> SEQUENCE: 4

Met Lys Arg Asp Leu His Gln Phe Gln Gly Pro Asn His Gly Thr Ser
1               5                   10                  15

Ile Ala Gly Ser Ser Thr Ser Ser Pro Ala Val Phe Gly Lys Asp Lys
            20                  25                  30

Met Met Met Val Lys Glu Glu Asp Asp Glu Leu Leu Gly Val Leu
        35                  40                  45

Gly Tyr Lys Val Arg Ser Ser Glu Met Ala Glu Val Ala Leu Lys Leu
    50                  55                  60

Glu Gln Leu Glu Thr Met Met Gly Asn Ala Gln Glu Asp Gly Leu Ala
65                  70                  75                  80

His Leu Ala Thr Asp Thr Val His Tyr Asn Pro Ala Glu Leu Tyr Ser
                85                  90                  95

Trp Leu Asp Asn Met Leu Thr Glu Leu Asn Pro Ala Ala Thr Thr
            100                 105                 110

Gly Ser Asn Ala Leu Asn Pro Glu Ile Asn Asn Asn Asn Asn Ser
        115                 120                 125

Phe Phe Thr Gly Gly Asp Leu Lys Ala Ile Pro Gly Asn Ala Val Cys
130                 135                 140

Arg Arg Ser Asn Gln Phe Ala Phe Ala Val Asp Ser Ser Ser Asn Lys
145                 150                 155                 160

Arg Leu Lys Pro Ser Ser Pro Asp Ser Met Val Thr Ser Pro Ser
                165                 170                 175
```

```
Pro Ala Gly Val Ile Gly Thr Thr Val Thr Val Thr Glu Ser Thr
            180                 185                 190

Arg Pro Leu Ile Leu Val Asp Ser Gln Asp Asn Gly Val Arg Leu Val
            195                 200                 205

His Ala Leu Met Ala Cys Ala Glu Ala Val Gln Ser Ser Asn Leu Thr
            210                 215                 220

Leu Ala Glu Ala Leu Val Lys Gln Ile Gly Phe Leu Ala Val Ser Gln
225                 230                 235                 240

Ala Gly Ala Met Arg Lys Val Ala Thr Tyr Phe Ala Glu Ala Leu Ala
            245                 250                 255

Arg Arg Ile Tyr Arg Leu Ser Pro Pro Gln Thr Gln Ile Asp His Ser
            260                 265                 270

Leu Ser Asp Thr Leu Gln Met His Phe Tyr Glu Thr Cys Pro Tyr Leu
            275                 280                 285

Lys Phe Ala His Phe Thr Ala Asn Gln Ala Ile Leu Glu Ala Phe Glu
            290                 295                 300

Gly Lys Lys Arg Val His Val Ile Asp Phe Ser Met Asn Gln Gly Leu
305                 310                 315                 320

Gln Trp Pro Ala Leu Met Gln Ala Leu Ala Leu Arg Glu Gly Gly Pro
            325                 330                 335

Pro Ser Phe Arg Leu Thr Gly Ile Gly Pro Pro Ala Ala Asp Asn Ser
            340                 345                 350

Asp His Leu His Glu Val Gly Cys Lys Leu Ala Gln Leu Ala Glu Ala
            355                 360                 365

Ile His Val Glu Phe Glu Tyr Arg Gly Phe Val Ala Asn Ser Leu Ala
            370                 375                 380

Asp Leu Asp Ala Ser Met Leu Glu Leu Arg Pro Ser Glu Thr Glu Ala
385                 390                 395                 400

Val Ala Val Asn Ser Val Phe Glu Leu His Lys Leu Leu Gly Arg Thr
            405                 410                 415

Gly Gly Ile Glu Lys Val Phe Gly Val Val Lys Gln Ile Lys Pro Val
            420                 425                 430

Ile Phe Thr Val Val Glu Gln Glu Ser Asn His Asn Gly Pro Val Phe
            435                 440                 445

Leu Asp Arg Phe Thr Glu Ser Leu His Tyr Tyr Ser Thr Leu Phe Asp
            450                 455                 460

Ser Leu Glu Gly Ala Pro Ser Ser Gln Asp Lys Val Met Ser Glu Val
465                 470                 475                 480

Tyr Leu Gly Lys Gln Ile Cys Asn Leu Val Ala Cys Glu Gly Pro Asp
            485                 490                 495

Arg Val Glu Arg His Glu Thr Leu Ser Gln Trp Ser Asn Arg Phe Gly
            500                 505                 510

Ser Ser Gly Phe Ala Pro Ala His Leu Gly Ser Asn Ala Phe Lys Gln
            515                 520                 525

Ala Ser Thr Leu Leu Ala Leu Phe Asn Gly Gly Glu Gly Tyr Arg Val
            530                 535                 540

Glu Lys Asn Asn Gly Cys Leu Met Leu Ser Trp His Thr Arg Pro Leu
545                 550                 555                 560

Ile Thr Thr Ser Ala Trp Lys Leu Ser Ala Val His
            565                 570

<210> SEQ ID NO 5
<211> LENGTH: 6
```

```
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (3)..(3)
<223> OTHER INFORMATION: Xaa = Arg or Asn

<400> SEQUENCE: 5

Gly Tyr Xaa Val Glu Glu
1               5

<210> SEQ ID NO 6
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (3)..(3)
<223> OTHER INFORMATION: Xaa = Arg or Asn
<220> FEATURE:
<221> NAME/KEY: MISC_FEATURE
<222> LOCATION: (6)..(6)
<223> OTHER INFORMATION: Xaa = any amino acid except Glu

<400> SEQUENCE: 6

Gly Tyr Xaa Val Glu Xaa
1               5

<210> SEQ ID NO 7
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (3)..(3)
<223> OTHER INFORMATION: Xaa = Arg or Asn
<220> FEATURE:
<221> NAME/KEY: MISC_FEATURE
<222> LOCATION: (6)..(6)
<223> OTHER INFORMATION: Xaa = any basic amino acid

<400> SEQUENCE: 7

Gly Tyr Xaa Val Glu Xaa
1               5
```

MUTANT GENE OF THE GRAS FAMILY AND PLANTS WITH REDUCED DEVELOPMENT CONTAINING SAID MUTANT GENE

FIELD OF THE INVENTION

The invention relates to the production of plants with reduced development, and in particular of crucifers.

BACKGROUND OF THE INVENTION

The use of dwarf plants in the context of agricultural production has many advantages; for example, in cereals, the use of short-straw mutant plants has made it possible to produce crops which tolerate considerable amounts of nitrogen-containing fertilizers, which are less affected by weather conditions and, in particular, more resistant to torrential rain than the plants which are normal in size. In addition, the small size of the plants facilitates the maintenance of the crops, in particular the application of plant-protection treatments, and also the harvesting thereof.

Dwarf mutants of plants other than cereals have also been described in the literature. Mention will in particular be made below of mutants which have characteristics similar to those induced by a deficiency in gibberellins and which are insensitive to the providing of exogenous gibberellins. Such mutants have in particular been described in *Arabidopsis* [Koornneef et al., Physiol. Plant., 65, 33-39, (1985)]. These mutants, named gai (for gibberellic acid insensitive) are smaller in size and do not respond to exogenous applications of gibberellins. The gai mutation is a semi-dominant mutation of the "gain of function" type. GAI/gai heterozygous mutants have an intermediate phenotype between that of gai/gai dwarf mutants and GAI/gai wild-type plants.

Mutants having the same characteristics as the gai mutants of *Arabidopsis* have been described by Zanewich et al. [J. Plant Growth Regul., 10, 121-127, (1991)], in *Brassica napus* (dwf1 mutation) and *Brassica rapa* (mutations named dwf1 and dwf2).

The team of the inventors has obtained a dwarf mutant of *B. rapa* [Foisset et al., Theor. Appl. Genet., 91, 756-761, (1995)]. The mutation, named bzh, has characteristics of "semi-dominance" and of insensitivity to gibberellins, which are similar to those of the gai mutation.

A rapeseed line, named ISN1770, homozygous for the bzh mutant allele, has been the subject of a Certificat d'Obtention Végétale [Plant Variety Protection Certificate] filed on May 18, 1998, with the CPOV [French Plant Variety Protection Office] (11 rue Jean Nicaud, 75007 Paris) under the reference 10751. A rapeseed hybrid, named "Lutin" (B017), comprising in its genome the bzh mutant allele in heterozygous form was proposed for listing in the Catalogue Français des Obtentions Végétales [French Catalogue of Plant Varieties] on Jul. 31, 1999, under the reference 072426.

The GAI gene of *Arabidopsis* has recently been cloned and sequenced [Peng et al., Genes and development, 11, 3194-3205 (1997); PCT application WO 97/29123 in the name of John Innes Centre Innovations Ltd.]. This gene-encodes a 532 aa protein (GAI). The gai allele, which is responsible for dwarfism, contains a deletion of 51 base pairs in frame with the reading frame, which leads to the absence of 17 aas located close to the N-terminal end of the GAI protein. The GAI protein is involved in the perception of and response to gibberellins, and is thought to act, in wild-type plants, as a negative regulator of cellular elongation in the absence of gibberellins.

Comparison of the GAI sequence with that of the translation products of other known genes has made it possible to place it in the family named GRAS [Pysh et al., The Plant Journal, 18(1), 11-119, (1999)] or VHIID [Schumacher et al., P.N.A.S., 96, 1, 290-295, (1999)].

This family encompasses, besides GAI, the RGA [Silvestrone et al., Genetics, 146, 1087-1099, (1998)] and SCARECROW [Di Laurenzio et al., Cell, 86, 423-433, (1996)] genes of *Arabidopsis*, and also the tomato LS (lateral suppressor) gene [Shumacher et al., P.N.A.S., 96, 1, 290-295, (1999)]. At the current time, about twenty genes belonging to the GRAS family have been identified in *Arabidopsis*.

The proteins which make the GRAS family have a very variable N-terminal portion and a very conserved C-terminal portion with five recognizable motifs, in particular the VHIID motif.

The biological functions of most of these proteins are not yet precisely known, but their role as transcription factors is strongly presumed. The investigations carried out on the 4 most thoroughly studied genes at the current time (SCR, GAI, RGA and LS), show that these genes encode transcription factors involved in controlling the perception of and the response to gibberellins, and indicate the probable importance of this family in controlling the morphogenesis and the development of higher plants.

BRIEF SUMMARY OF THE INVENTION

The inventors have now characterized and sequenced the BZH gene of *B. napus*, and its mutant allele bzh, associated with the dwarf phenotype previously observed by Foisset et al., (1995, abovementioned publication).

The sequence of the wild-type BZH gene is represented in the attached sequence listing under the number SEQ ID NO: 1, and the sequence of its translation product is represented under the number SEQ ID NO: 2. The sequence of the bzh mutant allele is represented in the attached sequence listing under the number SEQ ID NO: 3, and the sequence of its translation product is represented under the number SEQ ID NO: 4.

The coding region of the BZH gene is 1716 bps and the corresponding protein is 572 amino acids.

Analysis of the sequences of the BZH gene and of its translation product make it possible to place it in the GRAS family, and in particular in the subgroup comprising GAI, RGA and RGA-like. The alignment of the polypeptide sequences deduced from the BZH genes, with other genes of the GRAS family, namely the GAI, RGA, RGA-LIKE, SCARECROW and LS genes, is represented in FIG. 1.

Analysis of the sequences of the bzh mutant allele and of its translation product shows that the bzh mutation is a G→A substitution at position 1695 of the coding sequence. It leads to a glutamic acid→lysine amino acid change at position 546 of the polypeptide sequence.

Surprisingly, the bzh mutation is totally different from the gai mutation of *Arabidopsis*. In particular, while the gai mutation of *Arabidopsis* affects a region located in the N-terminal portion of the GAI protein, the bzh mutation affects a region located in the C-terminal portion of the BZH protein.

BRIEF DESCRIPTION OF THE DRAWINGS

Figure 1:
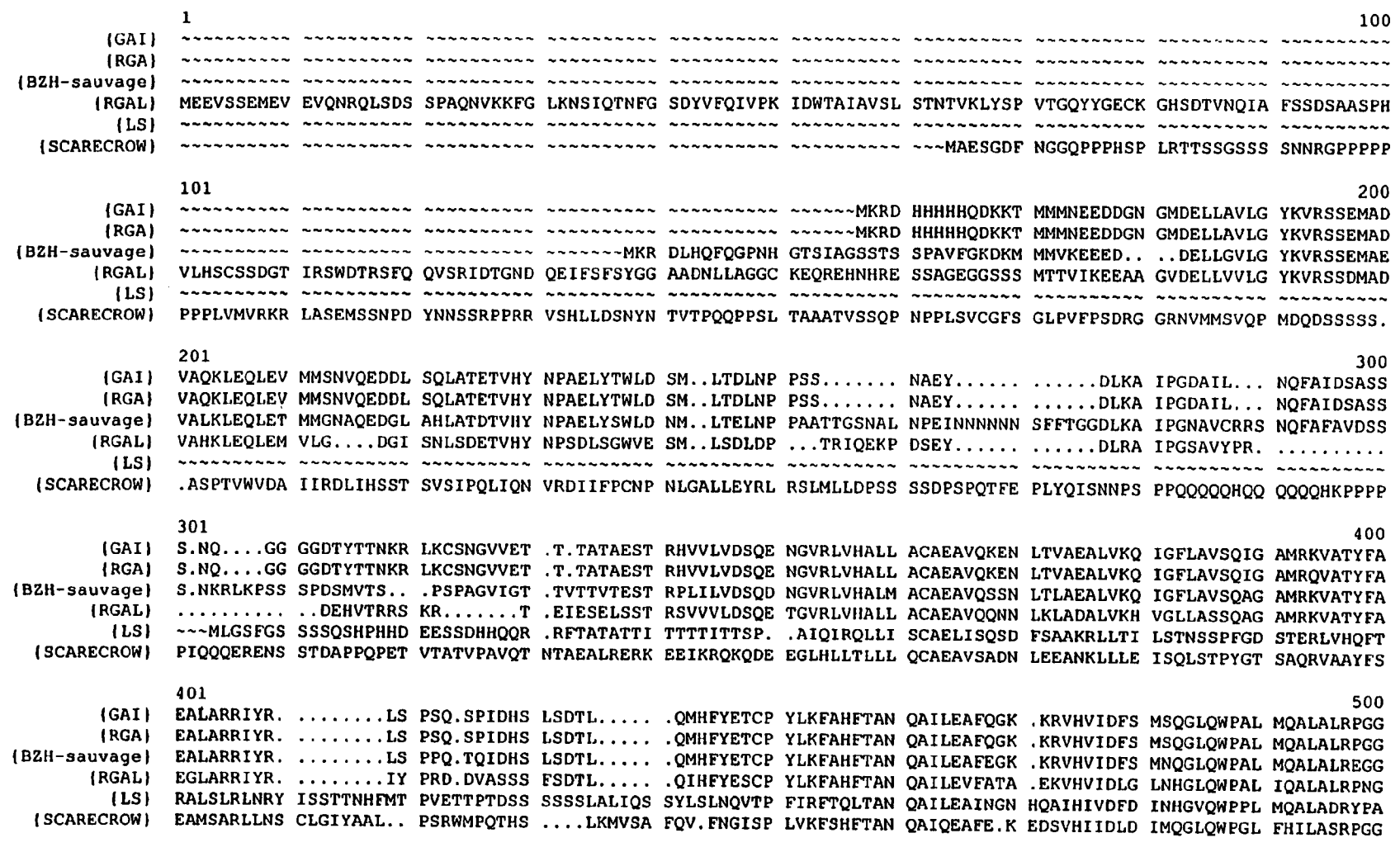

FIG. 1 represents an alignment of the polypeptide sequence deduced from the wild-type BZH gene with the polypeptide sequences deduced from other genes of the GRAS family namely the GAI, RGA, RGA-LIKE (RGAL), SCARECROW, and LS genes.

DETAILED DESCRIPTION OF THE INVENTION

A subject of the present invention is a nucleic acid sequence obtained by mutation of a sequence encoding a plant protein of the GRAS family comprising the following peptide sequence (I, SEQ ID NO:5):

Gly Tyr $X_1$ Val Glu Glu (I)

in which $X_1$ represents arginine or asparagine, characterized in that said mutation results in a modification of said sequence (I).

The expression "modification of the sequence (I)" is in particular intended to mean the substitution of one or more amino acids of said sequence, the insertion of one or more amino acids into this sequence, or the deletion of all or part of said sequence.

Plant proteins of the GRAS family comprising the peptide sequence (I) are in particular the BZH proteins of rapeseed, and also the proteins of the GAI or RGA subfamilies described above.

According to a preferred embodiment of a nucleic acid sequence in accordance with the present invention, it encodes a mutant protein comprising the following peptide sequence (II, SEQ ID NO:6):

Gly Tyr $X_1$ Val Glu $X_2$ (II)

in which $X_1$ is as defined above, and $X_2$ represents an amino acid other than glutamic acid. Advantageously, $X_2$ represents a basic amino acid, preferably a lysine.

The invention in particular encompasses the nucleic acid sequences encoding the polypeptide represented in the attached sequence listing under the number SEQ ID NO: 4, for example the sequence of the bzh mutant allele which is represented in the attached sequence listing under the number SEQ ID NO: 3.

A subject of the invention is also plants with reduced development, comprising one or more copies of a nucleic acid sequence in accordance with the invention.

This encompasses in particular:

mutant plants obtained from wild-type plants by conventional mutagenesis techniques, for example by treating seeds with a physical or chemical mutagen, selecting, from the plants derived from the treated seeds, the plants exhibiting dwarfism insensitive to gibberellins, and searching, among these plants, using conventional detection techniques of nucleic acid hybridization, for those which have a mutation in the nucleic acid sequence encoding the peptide sequence (I). It is also possible to introduce the desired mutation into a fragment, cloned beforehand, of the gene concerned and to reinsert the mutated sequence into the original gene as a replacement for the corresponding wild-type DNA;

transgenic plants obtained by transgenesis of a host plant with a nucleic acid sequence in accordance with the invention;

the descendants, possibly being obtained by sexual reproduction or vegetative multiplication, of the mutant plants or of the transgenic plants mentioned above.

Advantageously, plants in accordance with the invention are crucifers, and in particular Brassicacea, such as for example rapeseed, cabbage, turnip, brown mustard or Ethiopian mustard.

The plants expressing a nucleic acid sequence in accordance with the invention show, compared with the wild-type plants, a reasonably considerable reduction in size depending on the level of expression in said plant of the nucleic acid sequence in accordance with the invention. This level of expression in particular depends on the number of copies of the sequence. For example, in the case of rapeseed, the BZH/bzh heterozygous plants have an intermediate size between that of the dwarf bzh/bzh homozygous plants and that of the wild-type BZH/BZH plants.

The plants according to the invention have, in particular in the case of rapeseed, the following advantages:

the possibility of very early sowing, allowing the assimilation of nitrates, without the risk of stem elongation before winter;

better resistance to the cold;

better monitoring of the crop, due to a shorter size which facilitates plant-protection treatments;

very good resistance to torrential rain;

ease of harvesting.

The present invention will be more clearly understood with the aid of the further description which follows, which refers to nonlimiting examples describing the characterization of the rapeseed BZH gene and of a sequence in accordance with the invention derived from said gene.

EXAMPLES

Example 1

Characterization and Sequencing of the Wild-Type BZH Gene and of the Mutant BZH Gene The BZH gene was isolated on a 2352 base pair DNA fragment obtained from the "STELLAR" rapeseed line. This fragment contains a 1716 bps coding sequence, and the deduced polypeptide sequence is 572 amino acids. The coding sequence and the deduced polypeptide sequence are represented on the attached sequence listing under the numbers SEQ ID NO: 1 and 2, respectively.

In order to compare the sequence of the wild-type gene and of the bzh mutant allele, 5 lines were studied: wild-type PRIMOR (WTP), dwarf PRIMOR (DP), wild-type DARMOR (WTD), dwarf DARMOR (DD) and wild-type STELLAR (WTSTE).

The DNA fragments corresponding to the BZH locus were amplified on these lines, using primers derived from the sequence of SEQ ID NO: 1.

The comparison of the sequences of the amplification products obtained made it possible to establish that the only difference common to dwarf PRIMOR and dwarf DARMOR compared with the wild-type genotypes is a G→A substitution at position 1695 of the coding sequence. This substitution leads to a Glu→Lys amino acid change at position 546 of the peptide sequence.

The coding sequence carried by the nucleic acid fragment amplified from the dwarf primur line, and the corresponding peptide sequence, are represented in the attached sequence listing under the numbers SEQ ID NO: 3 and 4, respectively.

Example 2

Detection of the BZH Mutant Allele in Dwarf Plants 49 lines derived from the cross: dwarf DARMOR X YUDAL, and also the following pairs of [wild-type]/[bzh] isogenic lines: ISL1770/ISN1770, DOUBLOL/DOUBLOL-Bzh, GASPARD/GASPARD-Bzh and TAPIDOR/TAPIDOR-Bzh, were analyzed by PCR amplification of an approximately 400 bp region of the coding sequence, corresponding to the C-terminal portion of the protein, and polyacrylamide gel electrophoresis of the amplification products.

The lines with a "dwarf" phenotype exhibited, on the gel, a band characteristic of the presence of the G→A substitution.

The invention claimed is:

1. An isolated nucleic acid sequence encoding the polypeptide of SEQ ID NO: 4.

2. A plant with reduced development, comprising one or more copies of the nucleic acid sequence as claimed in claim 1.

3. The plant as claimed in claim 2, wherein it is crucifer.

4. The plant as claimed in claim 2, wherein it is a member of the family Brassicaceae.

5. The plant as claimed in claim 4, chosen from rapeseed, cabbage, turnip, brown mustard and Ethiopian mustard.

6. A mutant plant with reduced development, wherein said mutant plant is obtained by chemical mutagenesis and comprises one or more copies of a the nucleic acid sequence of claim 1.

7. The mutant plant of claim 6, wherein said mutant plant is a rapeseed plant.

8. A descendant of the mutant plant of claim 6, comprising one or more copies of said nucleic acid sequence.

* * * * *